US005747298A

United States Patent [19]

Hong et al.

[11] Patent Number: 5,747,298
[45] Date of Patent: May 5, 1998

[54] DNA POLYMERASE WITH PROOF-READING 3'-5' EXONUCLEASE ACTIVITY BACILLUS STEAROTHERMOPHILUS

[75] Inventors: Guo Fan Hong, Shanghai, China; Feng Zhai, deceased, late of Shanghai, China, by Fudi Ni, executor

[73] Assignee: Shanghai Institute for Biochemistry, Chinese Academy of Sciences, China

[21] Appl. No.: 544,643

[22] Filed: Oct. 18, 1995

[30] Foreign Application Priority Data

Nov. 17, 1994 [CN] China .................. 94-1-13990.5

[51] Int. Cl.$^6$ .................. C12P 19/34; C12N 9/12; C12N 1/20
[52] U.S. Cl. .................. 435/91.1; 435/194; 435/252.5; 435/6
[58] Field of Search .................. 435/194, 91.1, 435/252.5, 6

[56] References Cited

PUBLICATIONS

Bio–Rad, U.S. Bulletin 171, Fluorescent–Labeled DNA Sequencing Reactions Using Bst Polymerase,92–1362 1192, (date not availble).
Technical Bulletin, Promega, V. Sequence of pGEM®3z(+) Vector, Revised Feb. 1995, pp. 5–6.
Michael G. Riggs, Starla Tudor, Mathoor sivaram, Sherrol H. McDonough, Construction of Single Amino Acid Substitution Mutants of Cloned Bacillus stearothermophilus DNA Polymerase Which–Lacks 5'→3' Exonuclease Activity, Biochemica et Biophysica Acta 1307(1996) 178–186.
Jason M. Aliotta, John J. Pelletier, Jennifer L. Ware, Laurie S. Moran, Jack S. Benner, Huimin Kong, Thermostable Bst DNA Polymerase I Lacks a 3'→5'Proofreading Exonuclease Activity, Genetic Analysis Biomolecular Engineering, 12(1966) 185–195.
Sanger, et al., "DNA sequencing with chain–terminating inhibitors", Biochemistry: Proc. Natl. Acad. Aci. USA 74(197). pp. 5463–5467.
John Wiley & Sons, Inc., DNA Sequencing, Current Protocols In Molecular Biology, vol. 1, (1994).
Shengyu, et al., "Heat–Stable DNA Polymerase I Large Fragment Resolves Hairpin Structure in DNA Sequencing", Scientia Sinica (Series B) vol. XXX No. 5, May 1987, pp. 503–506.

Current Protocols in Molecular Biology, DNA Sequencing, 1972.
Epicentre Technologies, "DNA Polymerase (... fragment)", 1994/95 Products for Molecular & Cellular Biology.
Okazaki et al., "Enzymatic Synthesis of Deoxyribonucleic Acid", (1963), pp. 259–268.
Klenow, et al., "The N–Terminal Amino–Acid Sequences ... Proteolysis", Eur. J. Biochem. 45, pp. 623–627 (1974).
McClary, et al., "Sequencing with the large fragment .. .stearothermophilus" DNA Sequence–J DNA Sequencing and Mapping, vol.1, pp. 173–180, (1992).
McClary et al., "Bst DNA Polymerase Permits Rapid Sequence Analysis from Nanogram Amounts of Template", Research Report, vol. 11, No. 1 (1991), pp. 76–84.
Earley, et al., "Robotic Automation of Dideoxyribonucleotide Sequencing Reactions", Research Reports, vol. 17, No. 1 (1994) 156–165.
Mardis et al., "Automated Methods for Single–Stranded DNA Isolation and Dideoxynucleotide DNA Sequencing Reactions on a Robotic Workstation", Research Report, vol. 7, No. 8 (1989) pp. 840–850.
"What's new in this catalog?", Isotherm© DNA Polymerase (rBst DNA Polymerase large fragment), Epicentre Technologies Corporation, 1994, p. 1.
Bio Rad, "Premixed Nucleotide Sequencing Kits for Bst®DNA Polymerase", US Bulletin 1649, 1993.
ATCC Catalogue, Eighteenth Edition, 1992, p. 51
Kaboeu et al., J. Bact. vol. 145, No. 1, pp. 21–26, Jan. 1981.

*Primary Examiner*—Keith D. Hendricks
*Attorney, Agent, or Firm*—Cushman Darby & Cushman IP Group of Pillsbury Madison & Sutro, LLP

[57] ABSTRACT

The invention relates to a thermostable *Bacillus stearothermophilus* DNA polymerase which is capable of proofreading 3'–5' exonuclease activity during DNA sequencing of a DNA strand, such that the DNA polymerase functions to excise mismatched nucleotides from the 3' terminus of the DNA strand at a faster rate than the rate at which the DNA polymerase functions to remove nucleotides matched correctly with the nucleotides of the template, and which DNA polymerase does not exhibit 5'–3' exonuclease activity. The invention also relates to strains of *Bacillus stearothermophilus* capable of producing the thermostable DNA polymerase.

6 Claims, 2 Drawing Sheets

DNA POLYMERASE WITH PROOF-READING 3'-5' EXONUCLEASE ACTIVITY BACILLUS STEAROTHERMOPHILUS

BACKGROUND OF THE INVENTION

The genetic material of all known living organisms is deoxyribonucleic acid (DNA), except in certain viruses whose genetic material may be ribonucleic acid (RNA). DNA consists of a chain of individual deoxynucleotides chemically linked in specific sequences. Each deoxynucleotide contains one of the four nitrogenous bases which may be adenine (A), cytosine (C), guanine (G) or thymine (T), and a deoxyribose, which is a pentose, with a hydroxyl group attached to its 3' position and a phosphate group attached to its 5' position. The contiguous deoxynucleotides that form the DNA chain are connected to each other by a phosphodiester bond linking the 5' position of one pentose ring to the 3' position of the next pentose ring in such a manner that the beginning of the DNA molecule always has a phosphate group attached to the 5' carbon of a deoxyribose. The end of the DNA molecule always has an OH (hydroxyl) group on the 3' carbon of a deoxyribose.

DNA usually exists as a double-stranded molecule in which two antiparallel DNA strands are held together by hydrogen bonds between the bases of the individual nucleotides of the two DNA strands in a strictly matched "A-T" and "C-G" pairing manner. It is the order or sequence of the bases in a strand of DNA that determines a gene which in turn determines the type of protein to be synthesized. Therefore, the accurate determination of the sequence of the bases in a DNA strand which also constitutes the genetic code for a protein is of fundamental importance in understanding the characteristics of the protein concerned.

The process used to determine the sequence of the bases in a DNA molecule is referred to as DNA sequencing. Among the techniques of DNA sequencing, the enzymatic method developed by Sanger et al. (1) is most popular. It is based on the ability of a DNA polymerase to extend a primer annealed to the DNA template to be sequenced in the presence of four normal deoxynucleotide triphosphates (dNTPs), namely, dATP, dCTP, dGTP and dTTP, and on the ability of the nucleotide analogs, the dideoxynucleotide triphosphates (ddNTPs), namely, ddATP, ddCTP, ddGTP and ddTTP, to terminate the extension of the elongating deoxynucleotide polymers at various lengths.

In the classic one-step Sanger method, the sequence determination is carried out in a set of four separate tubes, each containing all four normal dNTPs, one of which is labeled with a radioactive isotope, $^{32}$P or $^{35}$S, for autoradiographic localization, a limiting amount of one of the four ddNTPs, a DNA polymerase, a primer, and the DNA template to be sequenced. As a result of the DNA polymerase activity, individual nucleotides or nucleotide analogs are added to the new DNA chains, all starting from the 3' end of the primer in a 5'-3' direction, and each linked to adjacent ones with a phosphodiester bond in a base sequence complementary to the DNA sequence of the template. Inasmuch as there is a nucleotide analog in the reaction mixture, each tube eventually contains numerous newly formed DNA strands of various lengths, all ending in a particular ddNTP, referred to as A, C, G or T terminator.

After resolving the four sets of reaction products by high-resolution polyacrylamide/urea gel electrophoresis, the populations of the newly formed DNA strands are separated and grouped according to their molecular weight. An autoradiographic image of the gel will show the relative positions of these DNA strands as bands which differ from one another in distance measured by one nucleotide in length, all sharing an identical primer and terminating with a particular ddNTP (A, C ,G or T). By reading the relative positions of these bands in the "ladder " of the autoradiograph, the DNA sequence of the template can be deduced.

The DNA polymerase used in the reaction mixture plays a pivotal role in DNA sequencing analysis. To be useful for DNA sequencing, a DNA polymerase must possess certain essential properties. For example, it must have its natural 5'-3' exonuclease activity removed by mutagenesis or by posttranslational modification, such as enzymatic digestion, and must be able to incorporate dNTPs and ddNTPs, without undue discrimination against ddNTP and with a sufficiently high processivity which refers to the ability of the enzyme to polymerize nucleotides onto a DNA chain continuously without being dislodged from the chain, and a sufficiently high elongation rate. A 5'-3' exonuclease activity associated with a DNA polymerase will remove nucleotides from the primer, thus cause a heterogeneous 5' end for the newly formed DNA strands, resulting in a false reading of the strand lengths on the sequencing gel. A DNA polymerase with a low processivity and a low elongation rate will cause many undesirable noise background bands of radioactivity due to the presence of DNA strands which are formed with improper lengths and improper terminations. Among the more commonly used DNA polymerases, Sequenase has a higher processivity and a higher elongation rate than others, such as the Klenow fragment, Taq, and Vent polymerases (2), and is therefore one of the most popular DNA polymerase selected for DNA sequencing to-date.

However, even when a DNA polymerase has been endowed with all the essential properties listed above, it may still generate erroneous or misleading band patterns of radioactivity in the sequencing gel. These artifactual patterns do not faithfully reflect the true nucleotide sequence in the template being sequenced. They may be caused by premature termination of the elongating strands due to the presence of secondary structures formed along the template, such as "hairpins" in the regions that contain palindromic sequences or that are rich in G and C bases (3); or, they may occur as a result of inadequate "proof-reading" function of the DNA polymerase that will allow the removal of misincorporated nucleotides at the 3' end of an elongating strand.

Researchers in the field of DNA sequencing often have to use several approaches to confirm their findings in order to avoid being misled by these potentially erroneous sequence data. For example, they sometimes rely on repeating the same sequencing experiment with different DNA polymerases, or performing another sequencing reaction with the template which is complementary to the first single-stranded DNA template, and compare the results for possible discrepancies.

Numerous investigators have tried to find an ideal DNA polymerase for enzymatic sequencing, i.e. an enzyme that not only has all the essential properties required for sequencing reaction, but also is capable of resolving the secondary hairpin structures and preventing the formation of strands containing nucleotides non-complementary to those of the template being sequenced.

The discovery by Ye and Hong (4) of the thermostable large fragment of DNA polymerase isolated from *Bacillus stearothermophilus*, an enzyme that is functional over the temperature range between 25° C. and 75° C., but is most active at 65° C., and possesses all the essential properties for DNA sequencing, has largely solved the problem caused by secondary structures in the template since these secondary structures are destabilized when the sequencing reaction is carried out at 65° C. In the past few years since this enzyme was made commercially available under the name of Bst DNA Polymerase (Bio-Rad Laboratories), independent reports have confirmed that during sequencing reaction catalyzed by this enzyme all four dNTPs, including dCTP, and other nucleotide analogs, such as dITP and 7-deaza-dGTP, are incorporated equally effectively in the chain elongation, thus eliminating the weak "C" band phenomena often observed when other DNA polymerases are used, and producing a very good band uniformity on the sequencing gel. It has been further established that at this elevated temperature Bst DNA Polymerase system can be used both for the classic Sanger one-step reaction as well as for the "labeling/termination" sequencing reaction, double-stranded DNA sequencing, and the incorporation of $^{35}$S-labeled nucleotides, and $^{32}$P-labeled nucleotides. Since this system can be placed at room temperature for at least two weeks without significant loss of its enzymatic activity, it has been adapted for automation of DNA sequencing which requires a stable DNA polymerase, using either fluorescent dye or radioactive isotope labeling.

One problem with the Bst DNA polymerase is its lack of 3'-5' exonuclease activity (5), and specifically, proof-reading 3'-5' exonuclease activity. A survey of the sequencing data collected from fourteen research centers which have used Bst DNA polymerase for their DNA sequencing work on over 120 DNA clones showed that, statistically, base pair mismatching occurs at a rate of about $1.5 \times 10^{-5}$. That is, approximately 1.5 errors can be expected in one hundred thousand nucleotide incorporations during nucleotide polymerization catalyzed by the enzyme.

It is generally known that the formation of incorrect DNA sequences due to mismatching of base pairs between the template and the growing nucleotide chain in DNA sequencing may be prevented by a 3'-5' exonuclease activity which "proof-reads" the nucleotide chain. However, even if a DNA polymerase exhibits 3'-5' exonuclease activity in vitro, it is often the case that the polymerase will not adequately "proof-read." Thus, the polymerase will not be capable of removing mismatched nucleotides from a newly formed DNA strand as efficiently as those nucleotides correctly matched with the nucleotides of the template. In other words, a 3'-5' exonuclease may excise the correctly matched nucleotides at a faster rate than the mismatched ones from the 3' terminus, or excise both the correctly matched and the mismatched nucleotides at the same rate. Consequently, even where the DNA polymerase has 3'-5' exonuclease activity, it does not perform any useful proof-reading function during DNA polymerization.

It is also known that a 3'-5' exonuclease activity associated with a DNA polymerase, in the presence of low concentrations of dNTPs, often counteracts the normal chain elongation process catalyzed by the polymerase, induces cyclic incorporation and degradation of nucleotides over the same segment of template, or even operates more efficiently than the polymerase activity per se, to the extent of causing degradation of the primer. Consequently, removal of the 3'-5' exonuclease activity along with the 5'-3' exonuclease activity from the native DNA polymerases by chemical means or by genetic engineering techniques has become a standard procedure in producing DNA polymerases for sequencing. This is a common strategy to preserve the essential properties of a DNA polymerase.

For example, among the major commercially available sequencing enzymes (other than the native Taq (Thermus aquaticus) DNA polymerase which lacks a 3'-5' exonuclease activity de novo) the 3'-5' exonuclease activity has been removed from the native T7 DNA polymerase, which lacks a 5'-3' exonuclease, either by a chemical reaction that oxidizes the amino acid residues essential for the exonuclease activity (Sequenase Version 1) or genetically by deleting 28 amino acids essential for the 3'-5' exonuclease activity (Sequenase 2).

Vent$_R$(exo$^-$) DNA polymerase, which is recommended as the preferred form of the Vent DNA polymerase for sequencing, also has its 3'-5' exonuclease activity removed by genetic modification. The native Vent DNA polymerase and the Klenow fragment isolated from the native E. coli DNA polymerase I possess a 3'-5' exonuclease; but these enzymes are no longer considered the enzymes of choice for DNA sequencing.

The Bst DNA polymerase isolated and purified from the cells of *Bacillus stearothermophilus* for DNA sequencing is free of 3'-5' exonuclease activity (5).

IsoTherm™ DNA Polymerase, a commercially available Bst DNA polymerase for DNA sequencing, marketed by Epicentre Technologies (1402 Emil Street, Madison, Wis. 53713), is also based on a Bst DNA polymerase whose 3'-5' exonuclease activity has been enzymatically removed.

Only the rBst DNA Polymerase produced from an over-expressing recombinant clone in *E. coli*, which is the product of the DNA pol I gene of *Bacillus stearothermophilus*, possesses a 3'-5' exonuclease activity in addition to a 5'-3' exonuclease activity. However, due to the existence of an undesirable 5'-3' exonuclease activity and a 3'-5' exonuclease activity of unknown characteristics, the latter product is not recommended by the company for DNA sequencing (6).

SUMMARY OF THE INVENTION

This invention addresses the above-described problems in the art by providing a novel Bst DNA polymerase which is capable of proof-reading 3'-5' exonuclease activity. In this invention, the term "proof-reading" is intended to denote that the Bst DNA polymerase is capable of removing mismatched nucleotides from the 3' terminus of a newly formed DNA strand at a faster rate than the rate at which nucleotides correctly matched with the nucleotides of the template are removed during DNA sequencing.

The invention also provides improved methods for DNA sequencing using the above-described Bst DNA polymerase. The invention also provides a test to screen for the Bst DNA polymerase in different strains of *Bacillus stearothermophilus* isolated from various sources.

Further objects and advantages of the invention will become apparent from the description and examples below.

DETAILED DESCRIPTION OF THE INVENTION

Figure 1:
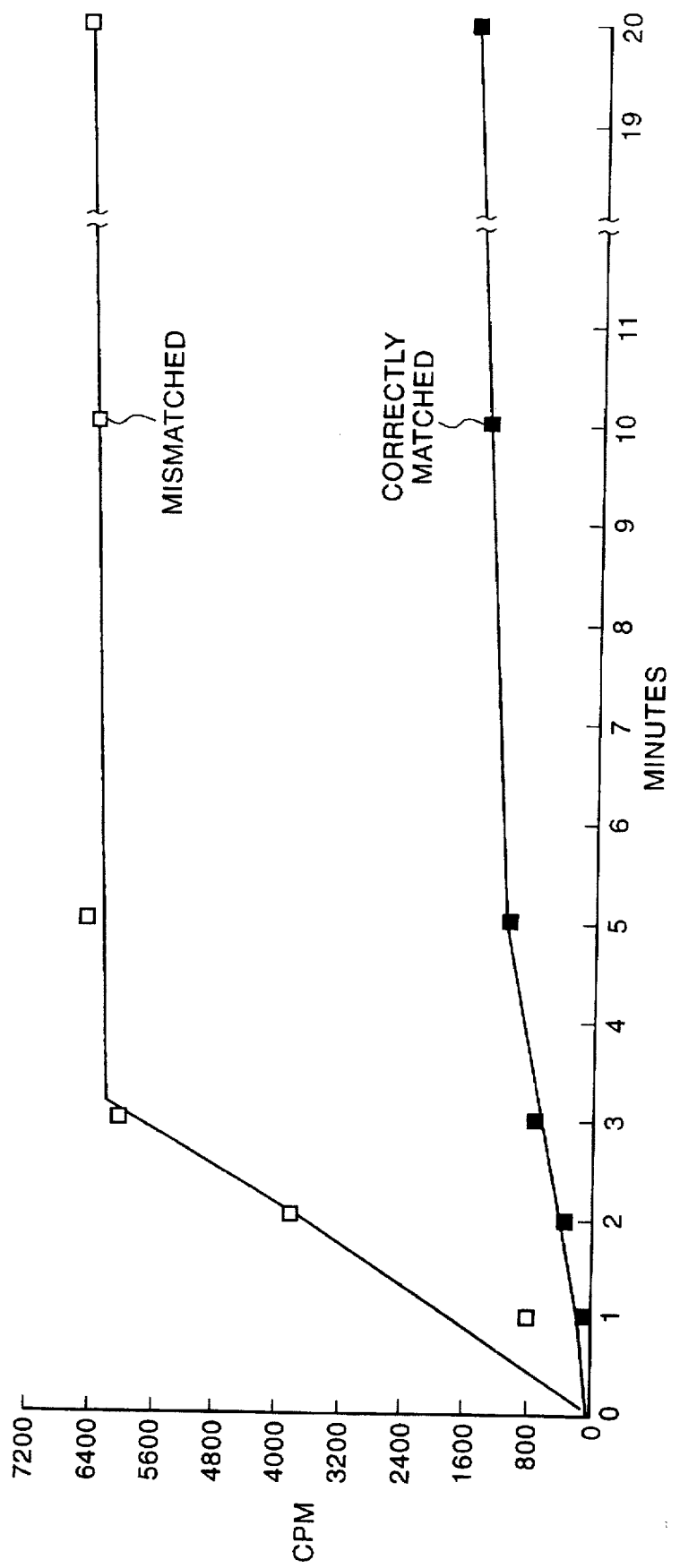
FIG. 1. This graph shows the excision of mismatched and correctly matched incorporated radio-labeled nucleotides expressed in CPM (counts per minute) from the 3' terminus by HiFi Bst DNA polymerase.

The DNA polymerase of the invention is extracted from *Bacillus stearothermophilus*, or is otherwise derived from

*Bacillus stearothermophilus*. The Bst DNA polymerase is capable of proofreading 3'–5' exonuclease activity, such that the DNA polymerase functions to excise mismatched nucleotides from the 3' terminus of the DNA strand at a faster rate than the rate at which nucleotides matched correctly with nucleotides of the template are removed, and which DNA polymerase does not exhibit 5'–3' exonuclease activity.

The invention also provides improved methods for DNA sequencing using the above-described Bst DNA polymerase. The methods entail sequencing a DNA strand by conventional protocols with the following modifications:

i) hybidizing a primer to a DNA template to be sequenced;
ii) extending the primer using a thermostable *Bacillus stearothermophilus* DNA polymerase described above, in the presence of nucleotide bases dATP, dGTP, dCTP and dTTP, or their analogs, and ddNTP chain terminators; and
iii) allowing a DNA strand to be sequenced.

The Bst DNA polymerase of the invention may be acquired using methods conventional in the art to screen and identify bacterial DNA polymerases with a proof-reading 3'–5' exonuclease activity for DNA sequencing. Preferably, the polymerase is obtained by segregating strains of *Bacillus stearothermophilus* into different groups according to the proof-reading exonuclease activity of their respective DNA polymerases.

As an example, the inventors have successfully purified from the cells of a strain of Bst (numbered Bst 320 for labeling purposes) a thermostable DNA polymerase from which the 5'–3' exonuclease activity was removed by digestion with subtilisin. The resultant enzyme possesses a proof-reading 3'–5' exonuclease activity which removes mismatched nucleotides from an elongating DNA strand at a higher rate than those correctly matched with the template. This new enzyme is distinguishable from the Bst DNA polymerase which does not have a 3'–5' exonuclease activity.

Similar to the known Bst DNA polymerase which has been well characterized by one of the inventors (4), the Bst DNA Polymerase of the invention (large fragment) has an apparent molecular weight of about 75,000 daltons, and has no 5'–3' exonuclease activity. It is functional in temperatures between 25° C. and 75° C., and is most active at 65° C. Thus, it is capable of overcoming the hindrance of secondary structures along the single-stranded DNA templates in DNA sequencing.

All four dNTPs, including dCTP, are incorporated equally effectively in the chain elongation during sequencing reaction catalyzed by the Bst DNA polymerase of the invention with a high processivity and a high elongating rate. There is no "weak C band" phenomenon often observed when other DNA polymerases are used. In addition, the enzyme can incorporate nucleotide analogs, such as ddNTPs, dITP and 7-deaza-dGTP without undue discrimination, and it produces a very good band uniformity in the sequencing gel.

The Bst DNA polymerase of the invention can be used both in the classic Sanger one-step reaction as well as in the "labeling/termination" sequencing reaction, double-stranded DNA sequencing, and the incorporation of $^{35}$S-labeled nucleotides, and $^{32}$P-labeled nucleotides. Since the enzyme can be stored at room temperature for at least two weeks without significant loss of its enzymatic activity, it can be adapted for robotic automation of DNA sequencing which requires a stable DNA polymerase, using either fluorescent dye or radioactive isotope labeling.

This invention involves a new method to measure the proof-reading 3'–5' exonuclease activity of purified DNA polymerases. The method is useful to screen a large number of Bst strains to select a strain which produces a DNA polymerase with a high proof-reading 3'–5' exonuclease activity. For instance, the method to test the proof-reading 3'–5' exonuclease activity of DNA polymerase was carried out as follows.

A DNA primer and two DNA templates with following sequences were synthesized chemically, using a DNA synthesizer.

17-base primer    5' CATTTTGCTGCCGGTCA 3'

1 mg/ml

Template (a)  3'------GTAAAACGACGGCCAGTCTT------5'

10 mg/ml

Template (b)   3'-----GTAAAACGACGGCCAGTCGG-----5'

10 mg/ml

To produce the radiolabeled primer, 1 μl (1 μg) of primer, 5 μl (50 μg) of template (a), 1 μl of [α-$^{32}$P] dATP (800 Ci/mmole), 1 μl of dGTP (0.5 mM), 1 μl of Taq DNA polymerase (1 unit), and 1 μl of buffer consisting of 500 mM Tris-Cl, pH 9.0, and 150 mM $MgCl_2$, were mixed in a test tube and incubated in a 65 C. water bath for 5 minutes. The mixture was subject to alkaline denaturing gel electrophoresis. The radioactive band containing the 20-base nucleotide was isolated and dissolved in 12 μl of 10 mM Tris-Cl buffer, containing 1 mM EDTA, pH 8.0. The final product represents the following labeled 20-base primer.

5'  CATTTTGCTGCCGGTCAGA*A*   3'

(* = $^{32}$P labeled)

To produce radiolabeled primer-template complexes, 5 μl of the labeled primer was mixed with 10 μl of template (a) or template (b) respectively to form the following:

Complex (a)
   5' CATTTTGCTGCCGGTCAGA* A*  3'
   3' GTAAAACGACGGCCAGTCT  T  5'

Complex (b)
   5' CATTTTGCTGCCGGTCAGA* A*  3'
   3' GTAAAACGACGGCCAGTCG  G  5'

The free radiolabeled primer was removed through a G-50 Sephadex column.

An aliquot of complex (a) which had two correctly matched radiolabeled A*s at the 3' terminus of the primer, and an aliquot of complex (b) which had two mismatched A*s at the 3' terminus of the primer, were then pipetted into two individual vials of scintillation fluid and their radioactivity was measured in a scintillation counter, and both complexes were adjusted with buffer to a concentration containing the same molarity of incorporated [α-$^{32}$P] dAMP.

To perform the proof-reading 3'–5' exonuclease activity, 20 μl of complex (a) or complex (b), 8 μl reaction buffer consisting of 15 mM Tris-Cl and 15 mM $MgCl_2$, pH 8.5, 4 units of DNA polymerase, and enough water to make up a total volume of 40 μl were pipetted into a test tube and mixed well. The mixture was subdivided into aliquots of 3 μl each in 0.5 ml microcentrifuge tubes and was then covered with 3 μl paraffin in each tube. The microcentrifuge tubes were incubated in a 65° C. water bath. At 1, 2, 3, 5, 10, and 20 minutes, a pair of the microcentrifuge tubes were taken out from the water bath and the content of each tube was dotted onto a DE-81 Whatman filter paper. One of each pair of the filter papers was put in scintillation fluid directly and the radioactivity was counted in cpm value in a scintillation counter; the other was washed three times in 0.3M sodium phosphate buffer, pH 6.8 before being put into the scintillation fluid for counting.

The difference in radioactivity expressed in cpm value between the washed filter paper and the unwashed filter paper in each pair was interpreted as representing the relative quantity of labeled nucleotides excised by the 3'-5' exonuclease activity from the 3' terminus of the primer. A DNA polymerase that excised the radiolabeled nucleotides A*s from complex (b) more efficiently than from complex (a) possessed proof-reading 3'-5' exonuclease activity. A DNA polymerase that excised the radiolabeled nucleotides A*s from complex (a) faster than from complex (b), or at nearly the same rate, was interpreted as possessing a non-specific 3'-5' exonuclease activity which is considered unsuitable for DNA sequencing.

Using these methods, a strain of Bst was isolated from among the strains of *Bacillus stearothermophilus* from various sources which is distinguished in its fast growth rate. This strain reaches an optimum exponential growth within 3 hours for DNA polymerase production. The strain is also novel in its ability to produce a DNA polymerase with a proof-reading 3'-5' exonuclease activity. This strain of *Bacillus stearothermophilus* was labeled Bst No. 320. A deposit of *Bacillus stearothermophilus* 320 was made on Oct. 30, 1995 at the ATCC, 12301 Parklawn Drive, Rockville, Md. 20852 and was given a deposit number ATCC 55719.

As persons skilled in this art would appreciated, the strain of *Bacillus stearothermophilus* from which the thermostable DNA polymerase of the invention can be obtained is not limited to Bst No. 320. On the contrary, the polymerase may be derived from strains of *Bacillus stearothermophilus* including wild strains or mutant strains acquired by various means, including spontaneous mutation.

To prepare DNA polymerase, the cells of Bst No. 320 were grown at 55° C. in a liquid medium consisting of 1% polypeptone, 0.5% yeast extract and 0.5% NaCl, pH7.0–7.2. The 3 hr old cells were collected after centrifugation and suspended in 4 volumes of TME buffer (50 mM Tris-HCl, pH7.5, 10 mM b-mercaptoethanol, and 2 mM EDTA), containing 100 mg lysozyme and 23 mg phenylmethylsulphonylfluoride/ml. The cells were broken by sonication in ice. The supernatant was pooled after centrifugation at 28,000 rpm in a Spinco L 30 rotor.

The DNA polymerase was prepared according to Okazaki and Kornberg (7) with a slight modification and the large fragment of the DNA polymerase was obtained by partial digestion of the whole DNA polymerase with the proteinase subtilisin (type Carlsberg) basically according to Jacobsen et al. (8).

The detailed procedure for purification of the enzyme was previously published (4). Since this new Bst DNA polymerase possesses a proof-reading 3'-5' exonuclease activity, it was labeled HiFi Bst.

The HiFi Bst was subject to a test for proof-reading and non-specific 3'-5' exonuclease activities as described above. The results showed that the HiFi Bst excises the mismatched incorporated nucleotides from the 3' terminus of a double-stranded DNA at a high rate, reaching the plateau of hydrolysis in about 3 minutes, about 8 times more efficiently in the first 3 minutes of reaction than those correctly matched with the nucleotides of the template (FIG. 1).

The following non-limiting examples are illustrative of the invention.

Example of using the Bst DNA polymerase of the invention for DNA sequencing

The following example is based on the standard Sanger protocol for single-strand DNA sequencing, using the Bst DNA polymerase of the invention as the enzyme.

1. Into a 1.5 ml centrifuge tube, were pipetted the following: 1.0 µl of universal DNA sequence primer containing 2.5–5 ng DNA with the sequence of 5'-GTAAAACGACGGCCAGT-3', 7.0 µl of ssDNA template containing 250–500 ng DNA, and 2.0 µl of 5× reaction buffer consisting of 100 mM Tris-Cl, pH 8.5, and 100 mM $MgCl_2$.

2. The mixture was placed in a 75° C. water bath for 5 minutes, and then allowed to cool slowly to ambient temperature over the course of 5 minutes.

3. Into the tube, were added 1.5 µl [$\alpha$-$^{35}$S] dATP (1000 Ci/mmole) and 1.0 µl of the Bst DNA polymerase of the invention containing 1.0 unit of the enzyme in 20 mM $KH_2PO_4$, pH 6.8, 10 mM b-mercaptoethanol, 50% glycerol. The contents were mixed and microcentrifuged for 2–3 seconds.

4. An aliquot of 2.5 µl of the mixture was pipetted into each of four tubes containing 2.0 µl of one of the following mix solution, pre-warmed to 65° C.:
   A. 620 mM DATP, 62 µM dCTP, 62 µM dGTP, 62 µM dTTP, 25 µM ddATP in 1.5 mM Tris-Cl, 0.15 mM EDTA, pH 8.0
   C. 800 nM dATP, 8 µM dCTP, 80 µM dGTP, 80 µM dTTP, 50 µM ddCTP in 1.5 mM Tris-Cl, 0.15 mM EDTA, pH 8.0
   G. 800 nM dATP, 80 µM dCTP, 4 µM dGTP, 80 µM dTTP, 75 µM ddGTP in 1.5 mM Tris-Cl, 0.15 mM EDTA, pH 8.0
   T. 800 nM DATP, 80 µM dCTP, 80 µM dGTP, 8 µM dTTP, 150 µM ddTTP in 1.5 mM Tris-Cl, 0.15 mM EDTA, pH 8.0

5. After mixing and microcentrifugation for 2–3 seconds, all four tubes, labeled A, C, G, and T, respectively, were placed in a 65° C. water bath for 2 minutes (elongation-termination reaction).

6. Into each of the four tubes, 2 µl of chase solution containing 0.5 mM for each of the four dNTPs (DATP, dCTP, dGTP and dTTP) dissolved in water was added. After mixing, the tubes were microcentrifuged and placed in a 65° C. water bath for further incubation for 2 minutes.

7. The reaction in all four tubes was stopped by adding 4 µl of stop solution consisting of 95% deionized formamide, 10 mM EDTA, 0.05% xylene cyanole FF, and 0.05% bromophenol blue. The mixture was microcentrifuged, and loaded in denaturing high resolution polyacrylamide gel for electrophoresis.

Figure 2:
FIG. 2. This is a radioautograph of a sequencing gel obtained by using the Bst DNA polymerase of the invention. A sequence pattern with discrete and evenly labeled bands can be clearly seen.

8. An autoradiographic image of the sequencing gel obtained (FIG. 2).

In further tests of the Bst DNA polymerase of the invention, it has been demonstrated that the rate of mismatched base pair incorporation during DNA polymerization catalyzed by the enzyme was in the order of $7.8 \times 10^{-7}$. This is almost a 20-fold improvement in accuracy over the usual Bst DNA Polymerase, which has an error rate of approximately $1.5 \times 10^{-5}$ during DNA sequencing, as noted previously.

In addition, the Bst DNA polymerase of the invention retains all other advantageous properties of the usual Bst. It also is functional within the temperature range between 25°

C. and 75° C., and is most active at 65° C. All four dNTPs, including dCTP, and other nucleotide analogs, such as dITP and 7-deaza-dGTP, are incorporated equally effectively in the chain elongation (thus eliminating the weak "C" band phenomena) with an excellent band uniformity on the sequencing gel (FIG. 2).

The polymerase of the invention can be used both for the classic Sanger one-step reaction as well as for the "labeling/ termination" sequencing reaction, double-stranded DNA sequencing, and the incorporation of $^{35}$S-labeled nucleotides, and $^{32}$P-labeled nucleotides (9). It can be used for rapid sequence analysis using nanogram amounts of template (10), and for automation of DNA sequencing which requires a stable DNA polymerase (11), using either fluorescent dye or radioactive isotope labeling (12).

All references mentioned herein are incorporated by reference in their entirety.

REFERENCES

1. Sanger, F., Nicklen, S. & Coulson, A. R. Proc. Nat. Acad. Sci., U.S.A. 74: 5463–5467. 1977.
2. CURRENT PROTOCOLS IN MOLECULAR BIOLOGY, Ausubel, F. M. et. Al. (Editors) Vol. I., John Wiley & Sons, Inc. 1995. pp 7.4.17–7.4.24.
3. Ibid p. 7.4.31.
4. Ye, S. Y. & Hong, G. F., Scientia Sinica (Series B) 30: 503–506. 1987.
5. In Ref. 2, p. 7.4.18 Table 7.4.2.
6. EPICENTRE TECHNOLOGIES CATALOG.1994/95 Products for Molecular & Cellular Biology, Page 1, "What's new in this catalog?"
7. Okazaki, T. & Kornberg, A. J. Biol. Chem. 239: 259–268. 1964.
8. Jacobsen, H., Klenow, H. & Overgard-Hansen, K. Eur. J. Biochem. 45: 623–627. 1974.
9. McClary, J., Ye, S. Y., Hong, G. F. & Witney, F. DNA Sequence 1: 173–180. 1991.
10. Mead, D. A., McClary, J. A., Luckey, J. A., et Al. BioTechniques 11: 76–87. 1991.
11. Earley, J. J., Kuivaniemi, H. Prockop, D. J. & Tromp, G. BioTechniques 17: 156–165,1994.
12. Mardis, E. R. & Bruce, A. R. BioTechniques 7: 840–850. 1989.

What is claimed is:

1. An isolated strain of *Bacillus stearothermophilus* which produces a thermostable DNA polymerase which has proofreading 3'–5' exonuclease activity during DNA sequencing of a DNA strand from a template, such that the DNA polymerase functions to excise mismatched nucleotides from the 3' terminus of the DNA strand at a faster rate than the rate at which the DNA polymerase functions to remove nucleotides matched correctly with nucleotides of the template.

2. The isolated thermostable DNA polymerase produced by the strain of *Bacillus stearothermophilus* of claim 1, which has proofreading 3'–5' exonuclease activity during DNA sequencing of a DNA strand from a template, such that the DNA polymerase functions to excise mismatched nucleotides from the 3' terminus of the DNA strand at a faster rate than the rate at which the DNA polymierase functions to remove nucleotides matched correctly with nucleotides of the template.

3. The strain of *Bacillus stearothermophilus* of claim 1 which is Bst 320 ATCC55719.

4. An isolated thermostable *Bacillus stearothermophilus* DNA polymerase which has proofreading 3'–5' exonuclease activity during DNA sequencing of a DNA strand from a template, such that the DNA polymerase functions to excise mismatched nucleotides from the 3' terminus of the DNA strand at a faster rate than the rate at which the DNA polymerase functions to remove nucleotides matched correctly with nucleotides of the template.

5. The DNA polymerase of claim 4, which has a molecular weight of about 75,000 daltons.

6. A method of sequencing a DNA strand comprising the steps of:

i) hybridizing a primer to a DNA template to be sequenced;

ii) extending the primer using a thermostable *Bacillus stearothermophilus* DNA polymerase which has proofreading 3'–5' exonuclease activity, such that the DNA polymerase functions to excise mismatched nucleotides from the 3' terminus of the DNA strand at a faster rate than the rate at which the DNA polymerase functions to remove nucleotides matched correctly with nucleotides of the template, in the presence of nucleotide bases dATP, dGTP, dCTP and dTTP, or their analogs, and ddNTP chain terminators; and iii) sequencing a DNA strand.

* * * * *